US011881300B2

(12) United States Patent
Feiweier et al.

(10) Patent No.: US 11,881,300 B2
(45) Date of Patent: Jan. 23, 2024

(54) METHOD, SYSTEM, AND MEDICAL IMAGING SYSTEM FOR CREATING AN IMAGE OF AN EXAMINATION OBJECT AND THE USE OF SUCH IMAGES

(71) Applicant: Siemens Healthcare GmbH, Erlangen (DE)

(72) Inventors: Thorsten Feiweier, Poxdorf (DE); Carsten Prinz, Baiersdorf (DE); Michael Schneider, Erlangen (DE); Michael Zenge, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 424 days.

(21) Appl. No.: 16/676,508

(22) Filed: Nov. 7, 2019

(65) Prior Publication Data
US 2020/0143935 A1      May 7, 2020

(30) Foreign Application Priority Data
Nov. 7, 2018  (EP) ..................................... 18204937

(51) Int. Cl.
*G16H 30/40* (2018.01)
(52) U.S. Cl.
CPC .................................. *G16H 30/40* (2018.01)
(58) Field of Classification Search
CPC ........ G16H 10/60; G16H 50/20; G16H 15/00; G16H 40/67; G16H 40/20
(Continued)

(56) References Cited

U.S. PATENT DOCUMENTS

| 6,931,270 B2 * | 8/2005 | Daft ..................... A61B 8/4438 600/407 |
| 2004/0049106 A1 * | 3/2004 | Kanazawa ............. A61B 5/055 600/428 |

(Continued)

FOREIGN PATENT DOCUMENTS

| CN | 102498712 A | 6/2012 |
| CN | 102695068 A | 9/2012 |

(Continued)

OTHER PUBLICATIONS

C. West, Daniel Alexander. "The Development of Experimental Models for NMR Studies of Neuropathology." University of London, University College London (United Kingdom), 2003. (Year: 2003).*

(Continued)

*Primary Examiner* — Amber A Misiaszek
(74) *Attorney, Agent, or Firm* — Banner & Witcoff Ltd.

(57) ABSTRACT

The present disclosure relates to an imaging system for creating an image of an examination object comprising a system component and a control component. The system component has a component property that is able to assume a value in a first value range established by the imaging system. A corresponding system component of another imaging system comprises a corresponding component property with another value range with an overlap range with the first value range. The control component is embodied to control the use of the system component on the creation of the image, wherein the control component can be operated in a compatibility mode. In the compatibility mode, the control component is configured, on the creation of the image, to only allow values that lie within the overlap range for the component property of the system component.

15 Claims, 3 Drawing Sheets

Figure 1:
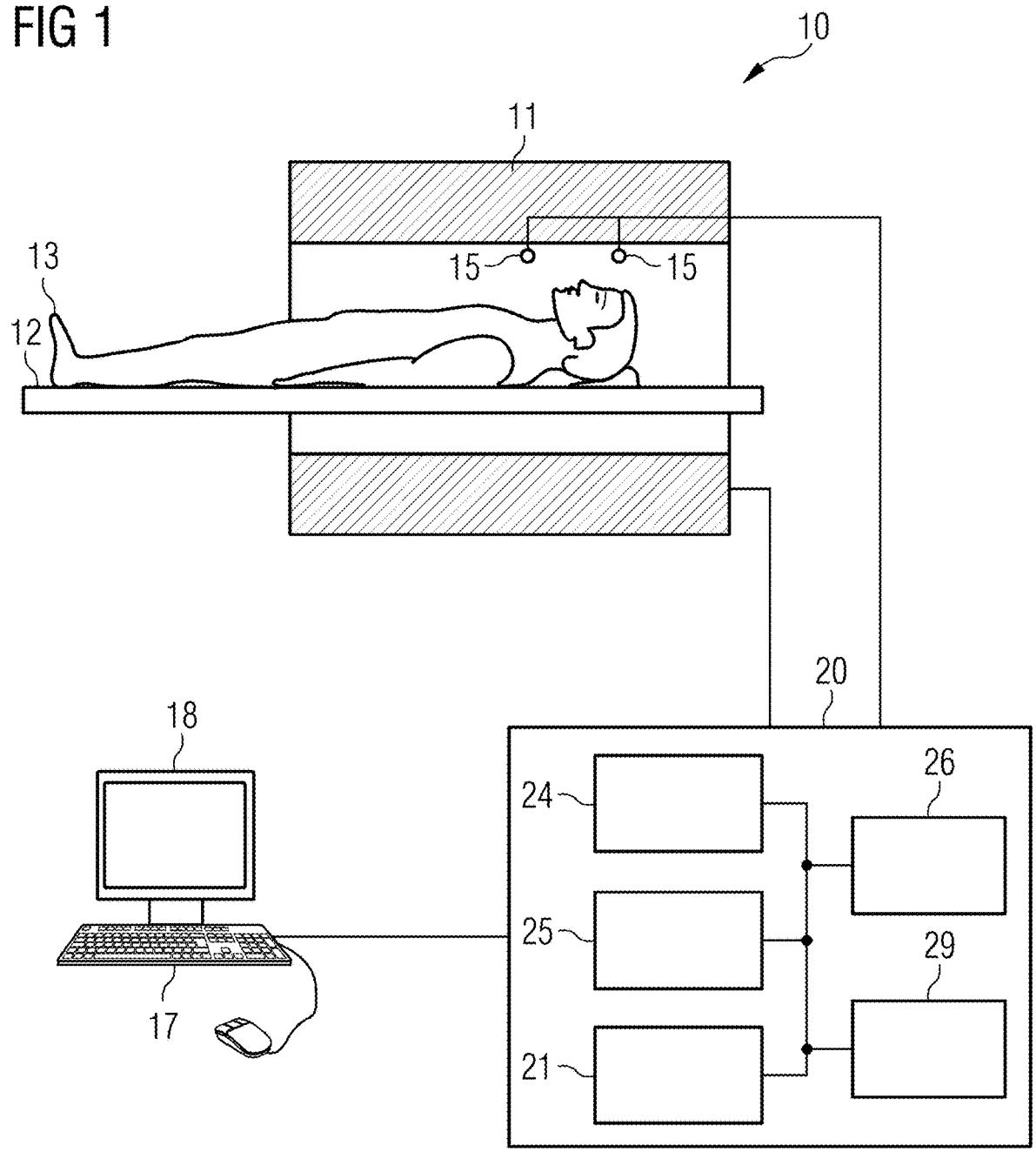

(58) Field of Classification Search
USPC .................................. 705/7.11–7.42
See application file for complete search history.

(56) References Cited

U.S. PATENT DOCUMENTS

| | | | | |
|---|---|---|---|---|
| 2004/0077952 | A1* | 4/2004 | Rafter | A61B 8/08 600/481 |
| 2004/0138923 | A1* | 7/2004 | Routh | G16H 40/67 705/2 |
| 2008/0033497 | A1* | 2/2008 | Bulkes | A61N 1/05 607/9 |
| 2009/0174405 | A1* | 7/2009 | Kassai | G01R 33/56572 324/309 |
| 2012/0041909 | A1 | 2/2012 | Glaser-Seidnitzer et al. | |
| 2012/0120249 | A1 | 5/2012 | Yoshizumi | |
| 2012/0242805 | A1 | 9/2012 | Tyou | |
| 2013/0181714 | A1* | 7/2013 | Umeda | G01R 33/56518 324/318 |
| 2015/0161340 | A1* | 6/2015 | Baumgart | G16H 50/20 705/2 |
| 2015/0355300 | A1* | 12/2015 | Ooshima | G01R 33/5608 324/309 |
| 2015/0356244 | A1 | 12/2015 | Seethamraju | |
| 2016/0045182 | A1* | 2/2016 | Stevens | A61B 6/5205 600/425 |
| 2016/0274782 | A1 | 9/2016 | Keil et al. | |
| 2017/0248669 | A1 | 8/2017 | Jasinschi et al. | |
| 2017/0322278 | A1 | 11/2017 | Ludwig | |
| 2018/0068070 | A1 | 3/2018 | Keil | |
| 2018/0306883 | A1 | 10/2018 | Meyer et al. | |

FOREIGN PATENT DOCUMENTS

| | | |
|---|---|---|
| CN | 105279364 A | 1/2016 |
| CN | 105982741 A | 10/2016 |
| DE | 102010034430 A1 | 2/2012 |
| DE | 112015004952 T5 | 9/2017 |
| DE | 102016207848 A1 | 11/2017 |
| DE | 102016216920 A1 | 3/2018 |
| EP | 3396572 A1 | 10/2018 |

OTHER PUBLICATIONS

European Search Report dated Apr. 30, 2019, for Application No. 18204937.9.

Feiweier et al. Method for providing MR scan protocols for different system configurations, Prior Art Journal 2018 #24, pp. 72-73, ISBN: 978-3-947591-02-2.

English Translation of European Search Report dated Apr. 30, 2019, for Application No. 18204937.9.

English translation of Extended European Search Report dated Apr. 30, 2019, for Application No. 18204937.9.

\* cited by examiner

METHOD, SYSTEM, AND MEDICAL IMAGING SYSTEM FOR CREATING AN IMAGE OF AN EXAMINATION OBJECT AND THE USE OF SUCH IMAGES

CROSS-REFERENCE TO RELATED APPLICATIONS

The present application claims the benefit of the filing date of European patent application no. EP18204937.9, filed on Nov. 7, 2018, the contents of which are incorporated herein by reference in its entirety.

TECHNICAL FIELD

The present disclosure is in the field of imaging and, in particular, relates to an imaging system for creating an image of an examination object, a medical imaging system, a method for determining an image of an examination object, and the use of images created in this way.

BACKGROUND

Usually, in order to create an image of an examination object, for example a patient in medical imaging, system components of an imaging system are controlled such that component properties of the system components assume specific values. Herein, the image created is dependent upon the respective imaging system and the values set in each case. In particular, in the case of medical imaging, the number of different types of imaging medical devices—such as various computed tomography or magnetic resonance tomography systems—continues to increase. As a result, different categories of customers are offered devices/systems adapted to their respective requirements. Herein, differentiating features can be performance or equipment features corresponding to specific component properties and values that can be assumed by the respective component property. MR systems (e.g. magnetic resonance tomography systems) are typically offered with different basic field strengths, different gradient field strengths and switching speeds, and different numbers of send or receive channels.

The scan protocols supplied for the respective imaging system are generally optimized to provide the desired diagnostic quality—for example contrast, resolution, signal-to-noise ratio etc.—or to enable the shortest possible recording times. For example, the recording time can be reduced by making full use of the available performance features—i.e. using component properties with values that are optimized for the respective application. For example, in the case of an MR system with a higher-performance, i.e. more powerful, gradient system or receiving system as a result of higher gradients—i.e. gradient values set in a higher range in the gradient system—an image can be created with a comparable image quality in a shorter time than is the case with another MR system with a less powerful gradient system.

However, the optimized scan protocols can have the result that images created with different imaging systems, for example in follow-up examinations, cannot be compared directly with one another, and individual measures to optimize the protocols—for example for one MR system and for another MR system—can result in different image appearances.

SUMMARY

There is a requirement to enhance imaging and improve reproducibility of an image appearance, i.e. of properties of an image created by means of imaging—for example for follow-up examinations in medical imaging and/or to increase efficiency when using a plurality of possibly different imaging systems.

The present disclosure achieves this object in accordance with the various embodiments described herein, which include an imaging system for creating an image of an examination object, a medical imaging system, a method for the determination of an image of an examination object, and by the use thereof in each case according to the teaching of one of the independent claims and other teachings as discussed herein. Advantageous embodiments, developments, and variants of the present disclosure may be found in the dependent claims and elsewhere throughout the present disclosure.

A first aspect of the present disclosure relates to an imaging system for creating an image of an examination object. The imaging system comprises a system component and a control component. The system component has a component property, which, on the creation of the image, is able to assume a value in a first value range established by the imaging system. Herein, a corresponding system component of another imaging system comprises a corresponding component property with another value range, with an overlap range that includes (e.g. overlaps with) the first value range. The control component is implemented to control the use of the system component on the creation of the image, wherein the control component can be operated in a compatibility mode. In the compatibility mode, the control component is configured, on the creation of the image, to only allow values that lie within the overlap range for the component property of the system component.

For the purposes of the present disclosure, a "component property" should be understood to mean at least a physical property or a functional property. For example, the system component can execute a specific function in/over the first value range and herein set a physical parameter on the creation of the image and/or induce a specific value for a physical quantity, such as a field strength. The system component can also, for example, execute a specific function using software, wherein specific implementations can be present or lacking in one imaging system or in another imaging system so that the one imaging system provides the specific implementation, while the other imaging system does not provide (or is unable to provide) this implementation. Herein, such software implementations or functions can in each case be characterized by a value so that the respective implementations or functions that are present—or also possible—define a value range and/or, conversely, the execution of the functions or implementations can be restricted to a subset, for example in an overlapping range of value ranges.

One advantage of only allowing values for the component property within the overlapping range can consist in the fact that the corresponding component property of the other imaging system can also assume such values. Thus, a scan protocol that effects the setting of such values can be executed on both systems, i.e. on the imaging system and the other imaging system, thus enabling more efficient use of the imaging systems. In addition, it is possible to achieve a comparable image appearance on the two imaging systems in that the same values are set for the component property. Consequently, the same scan protocol can be executed on the two different imaging systems—even without any previous conversion—thus enabling the different imaging systems to be used in dependence on their respective availability, and hence efficiently; this also enables the generation of consistent images of the examination object with the two different imaging systems and hence a consistent image appearance is obtained, thus, for example, enabling diagnosis based on such images in the case of medical imaging to be improved or and/or made easier.

According to some embodiments, the imaging system comprises an input facility that is configured based on the input of a user, to activate or deactivate the compatibility mode.

According to some embodiments, the imaging system comprises an output facility that is configured to output, e.g. by means of a user interface, the information whether or not the compatibility mode is activated. This advantageously enables a user to identify, for example before causing a scan protocol to be executed, whether the compatibility mode is active is or—in the event of a plurality of compatibility modes—which compatibility mode is active.

According to some embodiments, the control component can be operated in the compatibility mode or in a power mode. Herein, in the power mode, the control component is configured upon the creation of the image in the power mode to allow values of the component property of the system component that lie within the first value range but outside the overlapping range. This enables the quality of the imaging to be enhanced and/or the recording time required to create the image to be reduced compared to the creation of the image in the compatibility mode.

According to some embodiments, the control component can be operated in the compatibility mode or in a power mode. Herein, in the power mode, the control component is configured upon the creation of the image in the power mode to allow values of the component property of the system component that lie within the first value range but not necessarily outside the overlapping range. This enables scan protocols that use a wide range of possible values for the component property so that, for example, a user of the imaging system in the power mode has more freedom when using the imaging system, thus enabling fuller use to be made of the performance capacity of the imaging system.

In some embodiments in which the control component can be operated in a power mode, in the power mode, the control component is further configured to convert a scan protocol for the creation of the image for the compatibility mode into a scan protocol for the power mode and to execute the converted scan protocol. This advantageously enables scan protocols for the compatibility mode to also be executed in the power mode. Herein, in some variants, the control component is configured, during the conversion or the execution of the converted scan protocol, to also use values for the component property that lie outside the overlapping range, so that the possibly higher performance capacity in the power mode can also be used with converted scan protocols.

According to some embodiments, upon the conversion of a scan protocol, one or more parameters of the scan protocol can be adapted to the respective imaging system or to the respective compatibility mode.

According to some embodiments, the control component is further configured to convert a scan protocol that was not originally created for the compatibility mode—for example a scan protocol for a power mode—into a scan protocol for the compatibility mode, and to execute the converted scan protocol in the compatibility mode. This enables the use of further scan protocols in the compatibility mode, thus enabling increased efficiency during the operation of such imaging devices. In addition, in some variants, the control component is configured to store the converted scan protocol, thus enabling it to be executed on the imaging system and the other imaging system in the compatibility mode, e.g. without additional/repeated conversion.

For the conversion of a scan protocol for the compatibility mode into a scan protocol in another operating mode (e.g. the power mode), or for a conversion in the opposite direction, in some variants, the control component can be configured to execute a protocol conversion function. Herein, in some variants, the protocol conversion function can correspond to a so-called "phoenix function."

The protocol conversion function can be used for the automatic conversion of values from a combination of system components into values appropriate for the respective other operating mode. For example, with an MR system, lower achievable values for a gradient strength (e.g. gradient field strength or magnetic field strength) and/or a gradient rate of rise (e.g. rate of rise for short) can be at least partially compensated by correspondingly longer rise times or holding times. However, since the adapted scan protocol, i.e. the converted scan protocol, can cause an actual scan sequence to differ from an actual scan sequence with the original scan protocol, there may be differences in the creation of the image and hence a different image appearance. Nevertheless, the conversion can have an advantage in that a scan protocol can be used on different imaging systems, wherein the automatic conversion enables efficient use to be made of different imaging devices and/or keeps the resulting image appearance similar, as long the system components allow this.

In the context of the disclosure, a scan protocol, designated a so-called "phoenix function" or simply a functionality, is transferred from a first imaging system to another imaging system. As long as the system components of the other imaging system allow the protocol to be executed without changes, the protocol is used unchanged; otherwise, the protocol is automatically adapted to the performance capacity of the system components of the other imaging system.

In contrast to a so-called "phoenix function," the compatibility mode enables comparable—or even the same—image appearances to be achieved on different imaging systems on the creation of an image of an examination object, since the only values allowed for the component property of the system component are those which are possible for the respective imaging systems within the overlapping range (i.e. jointly and consequently), upon the creation of the image in the compatibility mode, only such values are allowed or set with respect to the component property. In this way, with some preferred variants, no conversion of the values to be set for the system component is necessary since the (common) compatibility mode guarantees that, on a transfer of such a scan protocol for the compatibility mode between two imaging systems, no adaptation of the scan protocol is required with this compatibility mode or the same compatibility class.

According to some embodiments, the control component is further configured to check whether, upon the creation of the image, the values to be set for the component property lie within the first value range and/or, at least in the compatibility mode, also lie within the overlapping range. Herein, the creation of the image is performed or is not performed in dependence of a result of the check and/or, if the values do lie within the first value range but outside the overlapping range, the image is created in a power mode and an error signal is output. If the creation is not performed, since the values to be set lie outside the first value range or outside the overlapping range, in some variants, the control component is configured to provide an error signal.

In some embodiments, the compatibility mode defines a first system-independent imaging system with a system-independent system component and a system-independent control component. The system-independent system component comprises a component property corresponding to component property of the system component of the imaging system and is able to assume a value in a system-independent value range lying entirely within the overlapping range. The system-independent control component is configured to execute a scan protocol for the compatibility mode and herein to set the value of the component property of the system-independent system component to one or more values in the system-independent value range.

In the compatibility mode, the control component of the imaging system is configured to provide a scan protocol to be executed for the creation of the image for the compatibility mode of the system-independent control component and to set the value of the component property of the system component using the value of the component property of the system-independent system component.

In some variants, the system-independent system component and/or the system-independent control component can be virtualized components, which, in a software implementation, abstract physical components so that, e.g. for software—based control—for example using a scan protocol—components of different physical imaging systems—for example the system component and the control component of the imaging system according to the first aspect of the disclosure—are represented in the same way. In addition, in some variants, the control component of the imaging system can be configured to execute a virtual machine for the system-independent control component and/or the system-independent system component. Such a compatibility mode with system-independent components advantageously enables the implementation of functions for controlling the imaging system (and further imaging systems) independently of the system, as a result of which it is possible to increase efficiency with the use of a plurality of (e.g. different) imaging systems and/or to improve reproducibility on the creation of images.

In some embodiments in which the compatibility mode defines a system-independent system component, the system-independent system component is configured to provide an interface between the system-independent control component and the system component of the imaging system, and herein to convert the values of the system component and the system-independent system component into one another. The control component is also configured to set values of the component property of the system component of the imaging system on the basis of the system-independent system component. This advantageously enables the system component of the imaging system, i.e. a physical component, to be controlled by means of the system-independent system component, wherein, in some variants, the values for the component property of the system-independent system component can be abstracted from the values of the component property of the (physical) system component. This makes it possible to achieve long-term compatibility between different generations of imaging systems.

According to some embodiments, the control component can be operated in the compatibility mode for a first system class including the imaging system and the other imaging system, and in a compatibility mode for a second system class including at least one further imaging system. Herein, a corresponding system component of the one further imaging system comprises a corresponding component property with a second value range so that the component property of the corresponding system component of the one further imaging system can assume a value in the second value range, wherein the second value range is established by the one further imaging system. One advantage of the two compatibility modes can in particular consist in the fact that different imaging systems can in each case be assigned to one or more of the compatibility modes and can hence in each case be operated by means of the control component in a compatibility mode with an overlapping range or value range that defines values that the respective component property of the respective system component can actually assume. In some variants, it is also possible for scan protocols to be created and/or optimized for the respective compatibility modes or converted from one of the compatibility modes into the respective other one.

In some embodiments in which the control component can be operated in a compatibility mode for a second system class, the overlapping range and the second value range are disjointed or only partially overlap.

In some embodiments in which the control component can be operated in a compatibility mode for a second system class, the control component is configured, upon the creation of the image, to convert values for the component property that lie within the second value range but outside the overlapping range into values that lie within the overlapping range.

In some embodiments in which the overlapping range and the second value range only partially overlap, the control component is configured, upon the creation of the image in the compatibility mode for the first system class, to only allow values for the component property of the system component that lie within the overlapping range. Additionally or alternatively, the control component is configured, upon the creation of the image in the compatibility mode for the second system class, to only allow values for the component property of the system component that lie in the first value range and simultaneously in the second value range.

In some embodiments in which the control component can be operated in a compatibility mode for a second system class, the second value range lies, e.g. entirely, within the overlapping range—i.e. in the value range in which the value ranges for the component properties of the system components of the first system class overlap. Here, advantageously, the compatibility mode for the first system class provides a compatibility mode for more powerful imaging systems, which therefore enable a larger value range, while the compatibility mode for the second system class provides an additional compatibility mode with imaging systems with a lower performance capacity, which therefore enable a smaller value range.

In some embodiments in which the control component can be operated in the compatibility mode for a first system class and in the compatibility mode for a second system class, both the first and the second system class include the imaging system according to the first aspect of the disclosure and the other imaging system, while the one further imaging system is not included in the first system class. Therefore, the compatibility mode for the second system class enables compatibility, and hence the same image appearance of images created via the compatibility mode for the second system class may be achieved for a larger number of imaging systems than for the compatibility mode for the first system class, which may include imaging systems with a higher performance capacity.

One advantage of the compatibility modes, e.g. a classification of system classes, which increasingly include further imaging systems, can include the fact that it is possible to create scan protocols in each case for a compatibility mode that is still appropriate, but which places comparatively the lowest requirements on the performance capacity of the imaging devices so that it is possible to achieve the same image appearance over a large number of imaging systems and/or to improve efficiency in the creation of scan protocols. Therefore, while it is possible to select a system class with correspondingly low requirements for the creation of images with low requirements, for higher requirements upon the creation of the image, it is possible to select a corresponding system class and a compatibility mode for these that allow values of the component property of the system component that lie outside the range for the system class with lower requirements.

According to some embodiments, the imaging system is embodied as a CT system (i.e. in particular as a computed tomography system).

According to some embodiments, the imaging system is embodied as an MR system (i.e. in particular as a magnetic resonance tomography system).

In some embodiments in which the imaging system is embodied as an MR system, the system component is a magnetic field gradient apparatus and the component property is a gradient field strength or a rate of rise, which is generated by the magnetic field gradient apparatus during the determination of the image. This enables a predetermined gradient moment with the same temporal field profile to be achieved for a trapezoidal slice excitation pulse and possible re-phasing with different MR systems, which are each operated in the compatibility mode, and hence increase the consistency of the image appearance.

In some variants, the component property or further component properties can include one or more of:
 a maximum gradient amplitude;
 a nominal gradient amplitude;
 a gradient rate of rise;
 gradient modeling;
 a maximum RF transmission field strength;
 a mean RF transmission field strength;
 RF transmission modeling;
 a number of RF transmit channels;
 a number of RF receive channels;
 an (existing/executable) software function;
 an (existing/provided/usable) hardware functionality such as, for example, a 3D camera for the acquisition of movements and/or for the correction of movements, an (absence) presence of specific RF receive coils or an (absence) presence of specific transmit coils;
 a patient model for SAR limitation;
 a patient model for nerve stimulation; or
 a combination thereof.

With some variants, the maximum gradient amplitude can advantageously be used to define a gradient field strength in a scan protocol for diffusion gradient pulses—often in "physical" coordinates and not in "logical" coordinates, which are based on the image orientation.

With some variants, the nominal gradient amplitude can advantageously be used to define a gradient field strength in a scan protocol in "logical" coordinates.

With some variants, a description of gradient field strengths by means of gradient modeling advantageously enables a complex description of the performance capacity of such an imaging system, for example how high the amplitude of gradient pulses can be with a specific temporal sequence so that they can be generated by the amplifiers. This is, for example, used with scan sequences operating in the boundary region of the hardware (for example diffusion measurements).

With some variants, the RF transmit modeling enables a more complex description of the performance capacity (e.g. taking into account the mean RF transmission field strength can enable simpler modeling).

With some variants, a higher number of transmit channels enables, for example, higher acceleration factors in the case of applications with "parallel transmission" (pTx) (this, for example, relates to two-dimensional or three-dimensional spatially selective excitation pulses).

With some variants, a higher number of receive channels enables higher acceleration factors with parallel imaging (for example GRAPPA, SENSE, CAIPIRINHA, etc.).

For example, with some variants, a software version can comprise additional functions, for example a first version may or may not support parallel imaging for 3D imaging, a subsequent version may support GRAPPA acceleration in one dimension and a further subsequent version may support GRAPPA (or CAIPIRINHA) acceleration in two dimensions, wherein in the compatibility mode, such functions are allowed that are available/possible on all imaging systems (of this system class).

With some variants, a patient model for nerve stimulation can advantageously be used to restrict the rates of change of the gradient fields (for example because of a regulatory restriction to avoid pronounced stimulation of the peripheral nerves), wherein, for example, the design of the gradient coil plays a role or advantageously the rates of rise of specific gradient pulses can be limited.

According to some embodiments, the control component is configured to convert a scan protocol for a compatibility mode—for example a compatibility mode for a first system class—into a scan protocol for another compatibility mode—for example a compatibility mode for a second system class—or vice versa. This enables scan protocols automatically to be used with different compatibility modes, thus enabling increased efficiency. With some variants with which the overlapping range and the second value range are disjointed, the automatic conversion of scan protocols or—alternatively or additionally—the provision of corresponding scan protocols for the respective other compatibility mode, can be particularly advantageous since, with respect to the values of their respective component property, the imaging systems of the first system class and the imaging systems of the second system class cannot be operated in an overlapping range, i.e. with the same values. However, (automatic) conversion, or possibly manually adapted scan protocols, enable these scan protocols to be optimized sufficiently to achieve an at least substantially identical image appearance with an image created by means of the respective scan protocol.

According to some embodiments, the system component has a further component property with values that cannot be harmonized with values of a corresponding further component property of the system component of the other imaging system, i.e. there is no common overlapping range. Herein, the control component can be operated in a hybrid compatibility mode as the compatibility mode or as a further compatibility mode. The control component is configured, on the creation of the image, to execute a hybrid scan protocol comprising at least one (sub-) scan protocol for the values of the further system component of the imaging system and a (sub-) scan protocol for the values of the further system component of the other imaging system, and for this to select and execute the appropriate scan protocol in each case (i.e. the (sub-) scan protocol for the values of the further system component of the imaging system). Herein, the two (sub-) scan protocols are matched to one another such that, upon their execution, these achieve a substantially identical image appearance even though the settable values for the respective further system component are different.

A second aspect of the disclosure relates to a medical imaging system with a first imaging system according to the first aspect and a second imaging system according to the first aspect. Herein, the first and the second imaging system are each embodied to determine an image of a patient as an examination object. In addition, the first value range established by the first imaging system is different from the other value range established by the second imaging system, wherein the first value range and the other value range comprise an overlapping range. Herein, the control component of the first and second imaging system can each be operated in a compatibility mode and, in this mode, configured to only allow values in this overlapping range.

The aforementioned advantages, embodiments, or variants of the first aspect of the disclosure also apply correspondingly to the medical imaging system.

A third aspect of the disclosure relates to a method for creating an image of an examination object by means of an imaging system, e.g. a group/fleet comprising a plurality of different imaging systems such as a medical imaging system. The imaging system comprises a system component having a component property that, upon the creation of the image, is able to assume a value in a first value range established by the imaging system. In addition, a corresponding system component of another imaging system, e.g. from the group/fleet, comprises a corresponding component property the values of which can assume another value range, wherein the other value range comprises an overlapping range with the first value range. The method comprises: the activation of a compatibility mode; and the creation of the image, wherein only values that lie within the overlapping range are allowed for the component property of the system component in the compatibility mode.

In some variants, the imaging system can be an imaging system according to the first aspect of the disclosure. In addition, in some variants, the group can comprise a plurality of imaging systems according to the first aspect of the disclosure. Additionally or alternatively, in some variants, the group or the medical imaging system can be a medical imaging system according to the second aspect of the disclosure.

In addition, in some variants, the method is executed on the imaging system and a control component operated therein by activation of the compatibility mode.

The aforementioned possible advantages, embodiments, or variants of the preceding aspects of the disclosure also apply correspondingly to the method according to the disclosure.

A fourth aspect of the disclosure relates to a use of an imaging system according to the first aspect of the disclosure, a medical imaging system according to the second aspect of the disclosure, or a method according to the third aspect of the disclosure for the creation of a plurality of images of one or more examination objects, wherein the images are processed by means of automatic image evaluation and/or used as training data for machine learning. One advantage of the use of the preceding aspects of the disclosure with automatic image evaluation or as training data for machine learning can include the fact that the compatibility mode guarantees a constant image appearance, thus enabling higher accuracy to be achieved with automatic image evaluation or making faster convergence or more robust modeling possible with training for machine learning.

The aforementioned possible advantages, embodiments, or variants of the preceding aspects of the disclosure also apply correspondingly to the use according to the disclosure.

In some embodiments, in the method for machine learning, e.g. by means of artificial neural networks, a plurality of images is created by means of at least one imaging system in the compatibility mode as training data and machine learning is performed on the basis thereof. The consistent image appearance enables one or more characteristics that are to be detected by the machine learning to be trained more easily and/or higher detection accuracies to be achieved.

It is also possible to obtain such training data using a greater number of corresponding imaging systems, which, although they have a common compatibility mode, may otherwise possibly differ from one another. This enables better use to be made of the imaging systems and/or training data to be obtained in a greater amount or more quickly than would be possible with only one type of imaging system—which, due to the fact that all imaging systems of this type are the same, would supply consistent imaging effects.

Methods, apparatuses, systems, and usages according to embodiments and the following examples enable the creation of images of one or more examination objects and herein can enable a consistent, e.g. the same, image appearance. Herein, some embodiments and/or some examples of the method can be executed at least partially in an automated manner. For this, in some embodiments and/or examples, an apparatus or a system or a part thereof can be configured to execute parts of a method automatically or parts of a method can be carried out automatically by means of these apparatuses, systems, or parts thereof.

For the purposes of the disclosure, "automatically" should at least be understood to mean that a part of a method, e.g. a method step or a process in the method and/or a functionality of an apparatus/system can be executed without human intervention.

The above-described features and features described below can be used not only in the corresponding combinations that are explicitly set out but also in further combinations or in isolation without departing from the scope of protection of the present disclosure.

Further advantages, features and possible applications may be derived from the following detailed description of exemplary embodiments and/or the figures.

The disclosure will be described in more detail with reference to advantageous exemplary embodiments. The same elements or components of the exemplary embodiments are substantially identified by the same reference characters unless stated otherwise or indicated otherwise by the context.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The present disclosure is described in detail below using embodiments according to the disclosure with reference to the figures. The exemplary embodiments of the present disclosure will be described with reference to the accompanying drawings. The drawing in which an element first appears is typically indicated by the leftmost digit(s) in the corresponding reference number.

Figure 2:
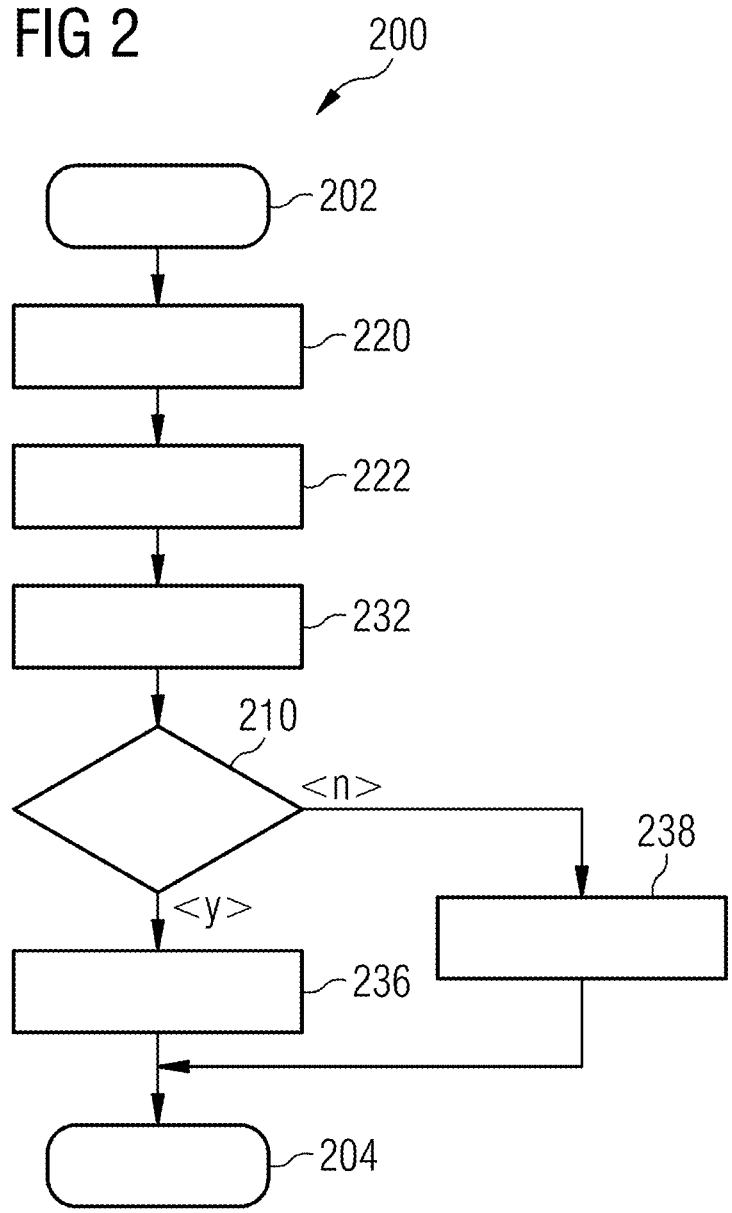
Figure 3:
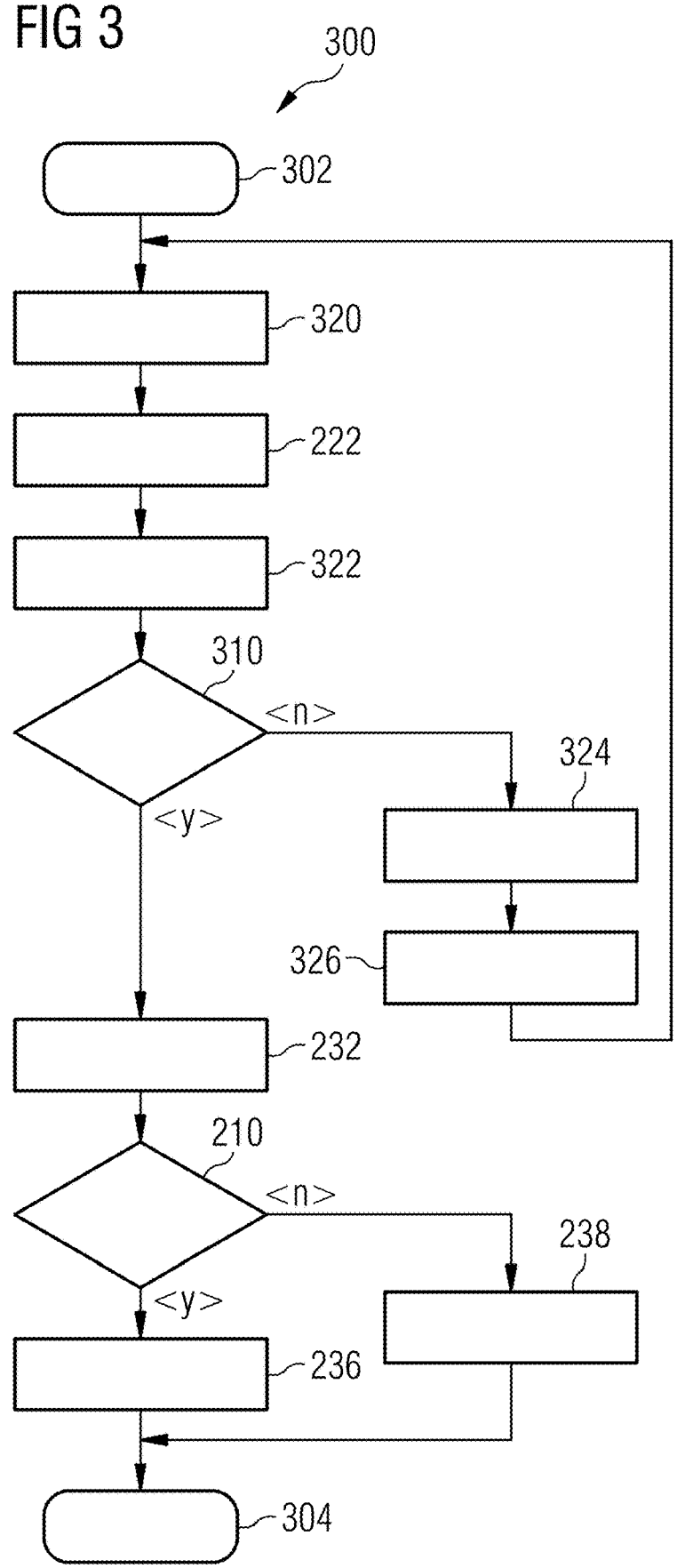

The figures show, partially in schematic form:

FIG. 1: a MR system according to an embodiment;

FIG. 2: a flow diagram of a method for creating an image of an examination object in a power mode according to an embodiment; and FIG. 3: a flow diagram of a method for creating an image of an examination object in a compatibility mode according to an embodiment.

DETAILED DESCRIPTION

The above-described properties, features and advantages of this disclosure and manner in which these are achieved will become clearer and more plainly comprehensible in conjunction with the following description of the exemplary embodiments explained in more detail in the context of the drawings.

The following describes the present disclosure with reference to various embodiments and with reference to the drawings. In the figures, the same reference characters refer to the same or similar elements. The figures are schematic representations of different embodiments of the disclosure. Elements depicted in the figures are not necessarily shown true to scale. Rather, the different elements depicted in the figures are reproduced in such a way that their function and general purpose become comprehensible to the person skilled in the art. Connections and couplings between functional units and elements that are depicted in the figures may also be implemented as an indirect connection or any suitable type of coupling. For instance, a connection or coupling may be implemented in a wired or wireless manner Functional units may be implemented as hardware, software, or a combination of hardware and software.

The figures are schematic depictions of different embodiments and/or exemplary embodiments of the present disclosure. Elements and/or components depicted in the figures are not necessarily shown true to scale. Instead, the different elements and/or components depicted in the figures are reproduced such that their function and/or their purpose can be understood by a person skilled in the art.

Connections and couplings depicted in the figures between functional units and elements can also be implemented as indirect connections or couplings. In particular, data connections can be embodied as wired or wireless, i.e. in particular as radio connections. In addition, specific connections, for example electrical connections, for example for the power supply, may not be depicted for purposes of clarity.

FIG. 1 is a schematic depiction of an imaging system 10 according to one embodiment of the present disclosure. Herein, the disclosure is explained below with reference to an imaging system embodied as an MR system by way of example and not limitation. In addition to the exemplary embodiments with reference to the MR system, the present description also discloses to the person skilled in the art how to execute the embodiments of the disclosure with other imaging systems such as, for example, a CT system or an ultrasound device by replacing specific details of the MR system by corresponding details, i.e. components and/or functions or processes with respect to the other imaging systems.

In one exemplary embodiment, the MR system 10 comprises a magnet 11 for generating a polarization field B0, wherein an examination subject 13—as the examination object—arranged on a bench 12 is moved into the magnet 11 in order to record spatially encoded magnetic resonance signals from the examination subject 13. The coils used to record the signals, such as a whole-body coil or local coils, are not depicted for purposes of clarity. The disclosure can be used with so-called parallel imaging with which the MR signals are recorded simultaneously with a plurality of local coils, i.e. a coil array of local coils. The radiation of radio-frequency pulses and switching of magnetic field gradients by means of gradient coils 15, e.g. RF coils as transmit coils and/or as receive coils, can cause the magnetization generated by the polarization field B0 to be deflected out of the equilibrium position and spatially encoded, with the resulting magnetization detected by the receive coils. Methods for generating MR images by radiating the RF pulses and switching magnetic field gradients in different combinations and sequences of MR images are known in principle to the person skilled in the art and thus will not be described in further detail here.

The MR system 10 further comprises a control component 20 that can be used to control the MR system. The control component 20 comprises a gradient control unit 25 for controlling and switching the necessary magnetic field gradients by means of the gradient coils 15. A RF control unit 24 is provided to control and generate the RF pulses for deflecting the magnetization. An image sequence controller 26 controls the sequence of magnetic field gradients, the signal detection and RF pulses, and hence indirectly the gradient control unit 25, the receive coils, and the RF control unit 24. An operator can control the MR system via an input unit 17, and MR images and other information required for control can be displayed on a display unit 18. A computing unit 29 with at least one processor unit (not shown) (e.g., one or more hardware processors and/or processing circuitry) is provided to control the different units in the control component 20. Also provided is a memory unit 21, in which, for example, program modules or programs can be stored, which, when they are executed by the computing unit 29 or its processor unit, can control the execution sequence of the MR system. For example, the memory unit 21 may include non-transitory computer-readable media having instructions stored thereon that, when executed by one or more processors (e.g., one or more processors associated with the computing unit 29), facilitate the MR system 10 to perform one or more embodiments as described in the present disclosure (e.g., the embodiments described with reference to FIGS. 2 and 3). Herein, in some variants, scan protocols can also be stored in the memory unit 21, wherein these can in turn control the execution sequence of the MR system and utilize any program modules or programs. As explained below, the control component 20, e.g. the computing unit 29, is implemented to be operated in a power mode and in a compatibility mode, wherein the control is dependent upon the respective operating mode.

The following explains the compatibility mode and the power mode with reference to three MR systems. Herein, one of the MR systems, for example the first MR system, can be implemented as an exemplary embodiment of the imaging system according to the disclosure, while the other MR systems, for example the second and the third MR system, can each be implemented as another imaging system. In some variants, the three MR systems can also be implemented as an exemplary embodiment of the medical imaging system, wherein, in addition to the first and second imaging system, this comprises a third imaging system, namely the third MR system.

The first MR system comprises as a system component a magnetic field gradient apparatus with the gradient coils 15 and the gradient control unit 25. The (maximum) achievable magnetic field strength with this magnetic field gradient apparatus is 60 mT/m and the (maximum) achievable rate of rise is 200 mT/m/ms. Correspondingly, the magnetic field strength and the rate of rise are, in each case, a component property of the system component, i.e. here the magnetic field gradient apparatus, which can in each case assume values in a first value range established by the MR system and, e.g., by the actual magnetic field gradient apparatus.

The second MR system also comprises a corresponding magnetic field gradient apparatus, wherein the achievable magnetic field strength is 45 mT/m and the achievable rate of rise is 100 mT/m/ms.

Finally, the third MR system also comprises a corresponding magnetic field gradient apparatus, wherein the achievable magnetic field strength is 30 mT/m and the achievable rate of rise is 100 mT/m/ms.

A scan protocol for creating an image of the examination subject 13 defines a trapezoidal slice excitation pulse, wherein, for this, the gradient amplitude is 20 mT/m and the plateau time is 3 ms. For a subsequent trapezoidal re-phasing pulse in the scan protocol, the zeroed gradient moment established from the middle of the slice excitation pulse has to be entirely re-phased.

First, there is a description of the execution sequence of the MR systems when they are operated in the respective power mode, thus enabling system-specific optimizations to be used in the scan protocol or during the execution of the scan protocol.

With the first MR system, the execution sequence in its power mode, is as follows:
rise to 20 mT/m at 200 mT/m/ms in 0.1 ms, 3 ms plateau time, 0.1 ms fall time; and
re-phasing of the moment of (20 mT/m*3 ms)/2+10 mT/m*0.1 ms=31 mT/m*ms with an amplitude gradient pulse of 60 mT/m, ramp time 0.3 ms and plateau time 0.22 ms;
resulting in a total duration of 0.1 ms+3.0 ms+0.1 ms+0.3 ms+0.22 ms+0.3 ms=4.02 ms.

With the second MR system, in its power mode, the execution sequence is as follows:
rise to 20 mT/m with 100 mT/m/ms in 0.2 ms, 3 ms plateau time, 0.2 ms fall time; and
re-phasing of the moment from (20 mT/m*3 ms)/2+10 mT/m*0.2 ms=32 mT/m*ms with an amplitude gradient pulse 45 mT/m, ramp time 0.45 ms and plateau time 0.26 ms;
resulting in a total duration of 0.2 ms+3.0 ms+0.2 ms+0.45 ms+0.26 ms+0.45 ms=4.56 ms.

With the third MR system, in its power mode, the execution sequence is as follows:
rise to 20 mT/m with 100 mT/m/ms in 0.2 ms, 3 ms plateau time, 0.2 ms fall time; and
re-phasing of the moment from (20 mT/m*3 ms)/2+10 mT/m*0.2 ms=32 mT/m*ms with an amplitude gradient pulse 30 mT/m, ramp time 0.3 ms and plateau time 0.77 ms;
resulting in a total duration of 0.2 ms+3.0 ms+0.2 ms+0.3 ms+0.77 ms+0.3 ms=4.77 ms.

There now follows a description of the execution sequence in the compatibility mode. Herein, the achievable magnetic field strengths of the system components (i.e. the magnetic field gradient apparatus of the three MR systems) have as an overlapping range a (maximum) achievable magnetic field strength of 30 mT/m. Furthermore, the achievable rates of rise of the system components (i.e. the magnetic field gradient apparatus of the three MR systems) have as an overlapping range a (maximum) achievable rate of rise of 100 mT/m/ms.

Hence, in the compatibility mode, the execution sequence is the same for all three MR systems, namely:
rise to 20 mT/m with 100 mT/m/ms in 0.2 ms, 3 ms plateau time, 0.2 ms fall time; and
re-phasing of the moment from (20 mT/m*3 ms)/2+10 mT/m*0.2 ms=32 mT/m*ms with an amplitude gradient pulse 30 mT/m, ramp time 0.3 ms and plateau time 0.77 ms;
resulting in a total duration of 0.2 ms+3.0 ms+0.2 ms+0.3 ms+0.77 ms+0.3 ms=4.77 ms.

Although, compared to the power mode, the total duration of the excitation is 19% longer with the first MR system and 5% longer with the second MR system, the same execution sequence can achieve the same image appearance. The advantage of the same image appearance can, for example for a diagnosis of the examination subject 13, outweigh a slightly prolonged recording duration that could result from the prolonged, total duration of the excitation. For instance, in everyday medical routine, in addition to the recording duration, further time may also be required for a diagnosis of the examination subject, for example for positioning the examination subject, for explanation, possibly for contrast agent injection, for planning the scan and/or for adjustments, etc. Hence, in some cases, the slightly prolonged recording duration can cease to be of significance. This can be the case, e.g., with the following applications: the creation of images of the spine, anatomical recordings, oncological recordings, and/or contrast-agent-enhanced MRI recordings providing they are not intended/required to acquire the contrast-agent dynamics.

On the other hand, for special applications with high hardware requirements, it may be advantageous to operate the MR system in the power mode in order to utilize the full performance capacity of the respective MR system. Such applications can, for example, include diffusion-tensor imaging, whole-body diffusion imaging or scans with high temporal resolution in the heart or after the administration of contrast agents (e.g. to acquire the dynamics of the contrast agent administration). Herein, full utilization of the performance capacity of the MR system can improve the quality of the diagnosis.

In everyday medical routines, it is also possible for the different MR systems to be divided into different system classes, each with a different performance capacity. For example, (virtually) all MR systems can be operated in the compatibility mode for a second system class with the lowest requirements for the performance capacity, wherein it is still possible for numerous basic diagnostic applications to be performed in this compatibility mode, e.g. routine applications such as, for example, anatomical imaging with T1, T2 or PD contrast in the brain, the spine, or the large joints—for example by means of TSE techniques—or even recordings for oncological purposes. On the other hand, some of the MR systems with a higher performance capacity can be (additionally) assigned to a first system class and these MR systems can be operated in a compatibility mode for the first system class, thus enabling special applications with high hardware-requirements in the compatibility mode for the first system class.

The MR system can also be configured automatically to take account of dependencies and limitations of scan parameters on the activation of the compatibility mode. For example, options which are only available with specific licenses or only with specific software versions—that provide specific software-implemented functions—and hence not on every MR system (including, for example, within a system class), can be automatically switched off and preferably replaced by alternatives available on the respective MR system. For example, two-dimensional CAIPIRINHA subsampling (Controlled Aliasing in Parallel Imaging Results in Higher Acceleration) could be replaced by one-dimensional GRAPPA subsampling (Generalized Autocalibrating Partially Parallel Acquisition). Herein, timing conflicts can be automatically resolved by prolonging time parameters such as, for example, TE or TR etc. It is also possible for options important for achieving a consistent image appearance to be adapted automatically, for example, image normalization or image filtering.

However, some component properties of system components of imaging systems, e.g. MR systems, cannot be harmonized by a (simple) compatibility mode. In the case of MR systems, this relates, for example, to the basic field strength, wherein for example, even with identical scan protocols and corresponding scan sequence/scan protocols, compared to MR systems with a basic field strength of 3 T, MR systems with a basic field strength of 1.5 T generate images with different contrast properties and hence establish a different image appearance.

In such cases, it is possible to provide two adapted compatibility modes or one (hybrid) compatibility mode with two corresponding scan protocols, which are optimized for the non-harmonizable component property such that, on the execution of these two optimized scan protocols to create an image of the examination subject 13 in each case, the same image appearance is achieved, at least substantially (e.g., within a matching tolerance such as 1%, 5%, 10%, etc.). For this, different parameters, which are, for example, dependent upon the basic field strength, such as, for example, echo times TE, repetition times TR, inversion times TI, or even the amount of averaging required, or possibly even entirely different scan techniques can be adapted with the two scan protocols. Such adaptations can be performed by means of automatic conversion, simulation-based optimizations and/or manually.

Herein, the two scan protocols for the two compatibility modes or for the one (hybrid) compatibility mode, which enables both scan protocols, are stored, thus achieving, at least in the respective compatibility mode or with the respective scan protocol, a consistent image appearance on different MR systems and achieving at least substantially the same image appearance with the respective other scan protocol, wherein the deviations in the image appearance are consistent. Accordingly, it is also possible to combine the two corresponding scan protocols to form one hybrid scan protocol from which it is then in particular possible to select the appropriate (sub-) scan protocol for the respective compatibility mode in each case. Especially in the case of MR systems with different basic field strengths, it is possible, for example in the case of MR systems with a basic field strength of 1.5 T, for conventional spin-echo imaging to be performed in the one scan protocol, while in the case of corresponding MR systems with a basic field strength of 3 T, inversion-prepared gradient-echo imaging is performed in the corresponding scan protocol.

One advantage of the two compatibility modes or the corresponding scan protocols can in particular consist in the fact that in each case an appropriate scan for the respective MR system (for example from a fleet of MR systems in a clinical network) can be selected automatically from the stored (corresponding) scan protocols and executed, thus increasing reliability on the creation of an image and improving the operational efficiency of such fleets or groups of MR systems.

FIG. 2 shows a flow diagram of a method 200 for creating an image of an examination object, for example an examination subject, by means of an imaging system, which is operated in a power mode, according to one embodiment of the present disclosure. The imaging system has a system component having a component property which on the creation of the image, is able to assume a value in a first value range established by the imaging system.

In one exemplary embodiment, the imaging system corresponds to the MR system described in respect of FIG. 1.

In one exemplary embodiment, the method 200 comprises the method steps 220, 222, 232, 236 and 238 and the method condition 210. The method 200 begins at the start of the method 202 and ends at the end of the method 204, wherein one or more method steps, in particular a sequence of method steps, and preferably the entire method can be executed repeatedly.

The method 200 may include activating (step 220) the power mode in the imaging system, such as the MR system, wherein, in some variants, for this purpose, a control component of the imaging system is operated in the power mode.

The method 200 may further include loading (step 222) a scan protocol for the power mode and for this purpose, for example, read from a memory unit 21.

The method 200 may further include performing (step 232) a check to determine whether values for the component property lie within the first value range. A check can be performed on the MR system to ensure the field strengths or rates of rise to be set do not exceed the maximal achievable field strength/rate of rise.

If the values to be set lie within the first value range, according to the method condition 210,—as symbolized there by <y>—the method step 236 is executed.

The method 200 may further include executing (step 236) the scan protocol such that the values of the component property are set in accordance with the scan protocol and in this way an image of the examination subject is created.

Otherwise, according to method condition 210—as symbolized by <n>—the method step 238 is executed.

The method 200 may further include outputting (step 238) an error signal to indicate that values to be set lie outside the (permissible) value range.

The method in which the imaging system is operated in the power mode, advantageously enables the performance capacity of the imaging system to be fully utilized while ensuring that no values outside the first value range, and hence no impermissible values, are set.

FIG. 3 depicts a flow diagram of a method 300 for creating an image of an examination object, for example an examination subject 13, by means of an imaging system in a compatibility mode according to one embodiment of the present disclosure. The imaging system comprises a system component having a component property which, upon the creation of the image, is able to assume a value in a first value range established by the imaging system. In addition, a corresponding system component of another imaging system comprises a corresponding component property of which the values can assume another value range, wherein the other value range comprises an overlapping range with the first value range.

In one exemplary embodiment, the imaging system corresponds to the MR system 10 explained in respect of FIG. 1.

In one exemplary embodiment, the method 300 comprises the method steps 222, 232, 236, 238, 320, 322, 324 and 326 and the method conditions 210 and 310. The method 300 begins with the start of the method 302 and ends with the end of the method 304, wherein one or more method steps, e.g. a sequence of method steps, and preferably the entire method can be executed repeatedly.

The method 300 may begin by activating (step 320), the compatibility mode. Herein, in some variants, a control component of the imaging system, for example the control component 20 of the MR system 10 according to FIG. 1, can be operated in the compatibility mode.

The method 300 may further include loading (step 222) a scan protocol for the compatibility mode.

The method 300 may further include performing (step 322) a check to determine whether values for the component property, which are to be set during the execution of the scan protocol, lie within the overlapping range.

If this not the case, according to the method condition 310—as symbolized there by <n>—method step 324 is performed first, then method step 326, and subsequently the execution of the method 300 is repeated again beginning with method step 320. Herein, in the method step 324, the scan protocol is converted so that now no values occur outside the overlapping range and, in the method step 326, this scan protocol is stored. Subsequently, following activation of the compatibility mode in the method step 320, the scan protocol converted and stored in this way can be loaded in the method step 222. Alternatively, following the conversion in the method step 324 or following the storage in the method step 326, the method could be continued in the method step 232 for the converted scan protocol. Alternatively, it would also be possible for an error signal to be output and the method ended or the method could be continued as described above.

If the values to be set lie within the overlapping range, according to method condition 310—as symbolized there by a <y>—the method step 232 is executed.

Herein, the sequence following method step 232 corresponds to the sequence in the method 200 as described with respect to FIG. 2.

One advantage of the method 300 in which the image is created in the compatibility mode can include the fact that the component property only assumes values that lie within the overlapping range, as a result of which it is possible to achieve a more consistent image appearance on different imaging systems, but which enable at least values within the overlapping range for the corresponding component property.

While exemplary embodiments were in particular described in detail with reference to the figures, reference is made to fact that numerous variations are possible. In addition, reference is made to the fact that the exemplary embodiments are only examples and are not intended to restrict the scope of protection, the application and the design in any way. Instead, the above description provides the person skilled in the art with a guide for the conversion of at least one exemplary embodiment, wherein diverse variations, in particular alternative or additional features and/or variations of the function and/or arrangement of the described components desired by the person skilled in the art can be performed without deviating from the subject matter defined in each case in the appended claims and/or departing from the scope of protection thereof.

What is claimed is:

1. A magnetic resonance (MR) imaging system for generating an image of an examination object, the MR imaging system comprising:
    magnetic field gradient circuitry having a component property which, to generate the image of the examination object, sets a value in a first value range established by the MR imaging system,
    wherein a further magnetic field gradient circuitry of a further MR system has a corresponding component property with a second value range established by the further MR imaging system; and
    gradient control circuitry configured to control the magnetic field gradient circuitry to generate the image of the examination object by operating in a compatibility mode in which the gradient control circuitry executes a scan protocol to only allow values to be set for the component property of the magnetic field gradient circuitry that lie within an overlap range that represents values of the first value range and the second value range that overlap with one another,
    wherein the component property of the magnetic field gradient circuitry includes values associated with a gradient field strength and a gradient rate of rise of the magnetic field gradients generated by the MR imaging system via the magnetic field gradient circuitry,
    wherein the gradient control circuitry and the further magnetic field gradient circuitry of the MR system and the further MR system, respectively, execute the same scan protocol when operating in respective compatibility modes such that the image of the examination object generated via the MR imaging system has the same image appearance as a further image of the examination object generated via the further MR imaging system, and
    wherein the scan protocol that is executed in accordance with the compatibility mode via the MR system and the further MR system defines a gradient amplitude, a plateau time, a ramp time, and a fall time for an excitation pulse and a corresponding re-phasing pulse.

2. The MR imaging system as claimed in claim 1, wherein:
    the gradient control circuitry is configured to operate in the compatibility mode or in a power mode; and
    when operating in the power mode, the gradient control circuitry is configured to generate the image of the examination object in the power mode by allowing[H] values to be set for the component property of the magnetic field gradient circuitry that lie within the first value range but outside the overlap range.

3. The MR imaging system as claimed in claim 2, wherein the gradient control circuitry is further configured to, in the power mode, (i) convert a scan protocol for the generation of the image of the examination object for the compatibility mode into a converted scan protocol for use in the power mode, and (ii) execute the converted scan protocol.

4. The MR imaging system as claimed in claim 2, wherein the gradient control circuitry is further configured to generate the image of the examination object, by verifying whether the values to be set for the component property lie within the first value range or lie within the overlap range, and
    wherein the generation of the image of the examination object is performed depending on a result of the verification such that, if the values lie within the first value range but outside the overlap range, the image of the examination object is generated in the power mode and an error signal is output.

5. The MR imaging system as claimed in claim 1, wherein:
the compatibility mode defines a system-independent MR imaging system with a system-independent magnetic field gradient circuitry and a system-independent gradient control circuitry;
the system-independent magnetic field gradient circuitry comprises a component property corresponding to the component property of the magnetic field gradient circuitry of the MR imaging system, and is able to only be set to one or more values in a system-independent value range that lie entirely within the overlap range;
the system-independent gradient control circuitry is configured to execute the scan protocol for the compatibility mode and to set the value of the component property of the system-independent magnetic field gradient circuitry to one or more values in the system-independent value range; and
the gradient control circuitry of the MR imaging system is configured to (i) provide the scan protocol to be executed for the generation of the image of the examination object for the compatibility mode of the system-independent gradient control circuitry, and (ii) set the value of the component property of the magnetic field gradient circuitry using the value of the component property of the system-independent magnetic field gradient circuitry.

6. The MR imaging system as claimed in claim 1, wherein:
the gradient control circuitry is configured to operate in (i) the compatibility mode for a first system class when the first system class comprises the MR imaging system and the further MR imaging system, and (ii) in a compatibility mode for a second system class when the second system class comprises at least one additional MR imaging system,
a corresponding magnetic field gradient circuitry of the at least one additional MR imaging system comprises a corresponding component property with the second value range established by the at least one additional MR imaging system, and
the component property of the corresponding magnetic field gradient circuitry of the at least one additional MR imaging system can only be set to one or more values in the second value range.

7. The MR imaging system as claimed in claim 6, wherein:
the second system class includes the MR imaging system;
the second value range lies at least partially within the overlap range thereby defining a second overlap range; and
in the compatibility mode for the second system class, the gradient control circuitry is configured to generate the image of the examination object to only allow values to be set for the component property of the magnetic field gradient circuitry that lie in the second overlap range.

8. The MR imaging system as claimed in claim 6, wherein:
the second system class does not include the MR imaging system;
the overlap range and the second value range partially overlap with one another; and
in the compatibility mode for the second system class, the gradient control circuitry is configured to generate the image of the examination object to only convert values for the component property that (i) lie within the second value range, but (ii) outside the overlap range, into values that lie within the overlap range.

9. The MR imaging system as claimed in claim 6, wherein:
the second system class includes the MR imaging system but does not include the further MR imaging system;
the overlap range and the second value range partially overlap with one another;
the first value range and the second value range at least partially overlap thereby defining a second overlap range; and
in the compatibility mode for the second system class, the gradient control circuitry is configured to generate the image of the examination object to only allow values to be set for the component property of the magnetic field gradient circuitry that lie in the second overlap range.

10. The MR imaging system as claimed in claim 1, wherein the first value range established by the MR imaging system is different from the second value range established by the further MR imaging system.

11. A method for generating an image of an examination object, the method comprising:
controlling, via gradient control circuitry to generate the image of the examination object, magnetic field gradient circuitry to set a component property to have a value in a first value range established by a magnetic resonance (MR) imaging system,
wherein a corresponding magnetic field gradient circuitry of a further MR imaging system has a corresponding component property with a second value range established by the further MR imaging system;
activating, via the gradient control circuitry, a compatibility mode in which the gradient control circuitry executes a scan protocol to generate the image of the examination object to only allow values to be set for the component property of the magnetic field gradient circuitry that lie within an overlap range that represents values of the first value range and the second value range that overlap with one another,
wherein the component property of the magnetic field gradient circuitry includes values associated with a gradient field strength and a gradient rate of rise of the magnetic field gradients generated by the imaging system via the magnetic field gradient circuitry, and
wherein the gradient control circuitry and the further magnetic field gradient circuitry of the MR system and the further MR system, respectively, execute the same scan protocol when operating in respective compatibility modes such that the image of the examination object generated via the MR imaging system has the same image appearance as a further image of the examination object generated via the further MR imaging system, and
wherein the scan protocol that is executed in accordance with the compatibility mode via the MR system and the further MR system defines a gradient amplitude, a plateau time, a ramp time, and a fall time for an excitation pulse and a corresponding re-phasing pulse.

12. A non-transitory computer readable media having instructions stored thereon that, when executed by one or more processors, cause the one or more processors to:
control, via gradient control circuitry to generate an image of an examination object, magnetic field gradient circuitry to set a component property to have a value in a first value range established by a magnetic resonance (MR) imaging system, wherein a corresponding magnetic field gradient circuitry of a further MR imaging system has a corresponding component property with a second value range established by the further MR imaging system, and activate, via the gradient control circuitry, a compatibility mode in which the gradient control circuitry executes a scan protocol to generate the image of the examination object to only allow values to be set for the component property of the magnetic field gradient circuitry that lie within an overlap range that represents values of the first value range and the second value range that overlap with one another, wherein the component property of the magnetic field gradient circuitry includes values associated with a gradient field strength and a gradient rate of rise of the magnetic field gradients generated by the imaging system via the magnetic field gradient circuitry, wherein the gradient control circuitry and the further magnetic field gradient circuitry of the MR system and the further MR system, respectively, execute the same scan protocol when operating in respective compatibility modes such that the image of the examination object generated via the MR imaging system has the same image appearance as a further image of the examination object generated via the further MR imaging system, and wherein the scan protocol that is executed in accordance with the compatibility mode via the MR system and the further MR system defines a gradient amplitude, a plateau time, a ramp time, and a fail time for an excitation pulse and a corresponding re-phasing pulse.

13. The MR imaging system of claim 1, wherein the gradient control circuitry is configured to operate in the compatibility mode to only allow values to be set for the component property of the magnetic field gradient circuitry that lie within the overlap range to enable the MR imaging system and the further MR imaging system to generate a predetermined gradient moment having the same temporal field profile.

14. The MR imaging system of claim 13, wherein the temporal field profile is associated with a trapezoidal slice excitation pulse.

15. The MR imaging system of claim 1, wherein the overlap range that represents values of the first value range and the second value range that overlap with one another comprises an overlapping range of achievable magnetic field strength between the MR system and the further MR system.

* * * * *